(12) United States Patent
Shimizu et al.

(10) Patent No.: US 11,331,366 B2
(45) Date of Patent: May 17, 2022

(54) COMPOSITION FOR SUPPRESSING MUSCULAR ATROPHY

(71) Applicant: OTSUKA PHARMACEUTICAL CO., LTD., Tokyo (JP)

(72) Inventors: Muneshige Shimizu, Osaka (JP); Akina Shiokawa, Osaka (JP); Koichiro Hamada, Osaka (JP); Kiyohiko Magata, Osaka (JP); Takeshi Nikawa, Tokushima (JP); Ayako Maita, Tokushima (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 181 days.

(21) Appl. No.: 16/466,488

(22) PCT Filed: Dec. 4, 2017

(86) PCT No.: PCT/JP2017/043452
§ 371 (c)(1),
(2) Date: Jun. 4, 2019

(87) PCT Pub. No.: WO2018/105550
PCT Pub. Date: Jun. 14, 2018

(65) Prior Publication Data
US 2019/0314443 A1    Oct. 17, 2019

(30) Foreign Application Priority Data
Dec. 5, 2016 (JP) .............................. JP2016-236099

(51) Int. Cl.
| A61K 38/05 | (2006.01) |
| A23L 33/18 | (2016.01) |
| A61P 21/00 | (2006.01) |
| A61K 38/06 | (2006.01) |

(52) U.S. Cl.
CPC ............ *A61K 38/05* (2013.01); *A23L 33/18* (2016.08); *A61K 38/06* (2013.01); *A61P 21/00* (2018.01)

(58) Field of Classification Search
CPC ......... A61K 38/05; A61K 38/06; A23L 33/18; A61P 21/00
See application file for complete search history.

(56) References Cited

U.S. PATENT DOCUMENTS

| 2009/0281174 A1 | 11/2009 | Ota et al. | |
| 2010/0210564 A1* | 8/2010 | Ohinata | ............. C07K 5/06043 514/1.1 |
| 2012/0070392 A1 | 3/2012 | Lee et al. | |
| 2012/0329991 A1 | 12/2012 | Miura et al. | |
| 2014/0105896 A1 | 4/2014 | Cload et al. | |
| 2015/0175654 A1* | 6/2015 | Choung | ............. C07K 5/06034 514/1.9 |
| 2016/0305933 A1 | 10/2016 | Shigemoto | |

FOREIGN PATENT DOCUMENTS

| EP | 2 813 224 A1 | 12/2014 | |
| JP | 6-256387 A | 9/1994 | |
| JP | 2001-089387 A | 4/2001 | |
| JP | 2002-338464 A | 11/2002 | |
| JP | 2006-213667 A | 8/2006 | |
| JP | 2006-328031 A | 12/2006 | |
| JP | 2008-013473 A | 1/2008 | |
| JP | 2008-501642 A | 1/2008 | |
| JP | 2012-522043 A | 9/2012 | |
| JP | 2014-141462 A | 8/2014 | |
| JP | 2015-530390 A | 10/2015 | |
| JP | 2016-160183 A | 9/2016 | |
| JP | 2016-193865 A | 11/2016 | |
| WO | 98/09985 A2 | 3/1998 | |
| WO | WO-9809985 A2 * | 3/1998 | ......... C07K 5/06104 |
| WO | 1998/023283 A | 6/1998 | |
| WO | WO/1998/023283 * | 6/1998 | .......... A61K 38/005 |
| WO | WO-9823283 A1 * | 6/1998 | ............ G01N 33/68 |
| WO | 2005/105832 A2 | 11/2005 | |
| WO | 2010/087480 A1 | 8/2010 | |
| WO | 2011/108692 A1 | 9/2011 | |
| WO | 2014/030514 A1 | 2/2014 | |
| WO | WO-2014047614 A1 * | 3/2014 | ............ A23L 33/12 |
| WO | 2015/060430 A1 | 4/2015 | |

OTHER PUBLICATIONS

Partial Translation of JP 2001-089387 A, published Apr. 3, 2001 (reference submitted Sep. 4, 2019).
Translation of JP 2016-193865 A, published Nov. 17, 2016 (reference submitted Sep. 4, 2019).
Murata T et al., "Production of poly(L-aspartyl-L-phenylalanine) in *Escherichia coli*", Journal of Biotechnology, vol. 28, No. 2-3, pp. 301-312, Apr. 1, 1993 (12 pages total).
Natalia Sánchez De Groot et al., "Ile-Phe Dipeptide Self-Assembly: Clues to Amyloid Formation", Biophysical Journal, vol. 92, No. 5, pp. 1732-1741, Mar. 1, 2007 (10 pages total).
Extended European Search Report dated Jun. 19, 2020 from the European Patent Office in EP Application No. 17878638.0.
Jung, J. et al., "A Tweezer-like Peptide binding Receptor", Bulletin of Korean Chemical Society, 2003, vol. 24, No. 10, pp. 1525-1526, ISSN:1229-5949 (2 pages total).
Kukman, I. L. et al., "Isolation of low-molecular-mass hydrophobic bitter peptides in soybean protein hydrolysates by reversed-phase high-performance liquid chromatography", Journal of Chromatography A, 1995, vol. 704, pp. 113-120 (8 pages total).

(Continued)

*Primary Examiner* — Fred H Reynolds
*Assistant Examiner* — Joseph Fischer
(74) *Attorney, Agent, or Firm* — Sughrue Mion, PLLC

(57) ABSTRACT

The present invention provides a composition for suppressing muscular atrophy, comprising as an active ingredient(s) one or more peptides selected from the group consisting of tripeptides DIY, IYN, YNP, NPQ, DFY, DIF, FYN, IFN, FNP, and NPK; the group consisting of dipeptides comprising F; and the group consisting of dipeptides DI, IY, YN, and NP.

11 Claims, 4 Drawing Sheets

(56) References Cited

OTHER PUBLICATIONS

International Search Report (ISR) dated Jan. 30, 2018, in International Application No. PCT/JP2017/043452.
International Preliminary Report on Patentability (IRPP) with translation of Written Opinion dated Jun. 11, 2019, in International Application No. PCT/JP2017/043452.
Hosaka et al., "dysuria", Clinic all-round, vol. 47, No. 1, 1998, pp. 66-69 (4 pages total).

* cited by examiner

COMPOSITION FOR SUPPRESSING MUSCULAR ATROPHY

CROSS REFERENCE TO RELATED APPLICATIONS

This application is a National Stage of International Application No. PCT/JP2017/043452 filed on Dec. 4, 2017, which claims priority from Japanese Patent Application No. 2016-236099 filed on Dec. 5, 2016.

TECHNICAL FIELD

The present application claims priority to Japanese patent application No. 2016-236099, which is incorporated herein in entirety by reference.

The present invention relates to a composition for suppressing muscular atrophy, comprising a dipeptide or a tripeptide as an active ingredient.

BACKGROUND ART

Muscle mass in humans over 30 years old has been reported to decrease at a rate of about 5% per 10 years and the rate of decrease accelerates over 60 years old. The atrophy of skeletal muscle is observed in age-related sarcopenia and also can be caused by inactivity (disuse, bed rest, casting) and weightlessness (outer space), denervation, diseases (such as cancer, AIDS, and diabetes), and malnutrition, besides the age-related sarcopenia. An event commonly observed in muscular atrophy is muscle fiber atrophy (decrease in muscle cross-sectional area) caused by decrease in muscle proteins by the imbalance of synthesis and degradation of muscle proteins.

Muscular atrophy can decrease ADL (activities of daily living) and QOL (quality of life), increase the risk of injury by fall and even disturb physical independence, ultimately becoming bedridden. Moreover, decrease in muscle mass reduces basal metabolism, which increases the risk of metabolic syndrome. Accordingly, suppression of muscular atrophy is a great issue for the whole nation.

High intensity resistance training in exercise has been confirmed to be effective for the prevention or improvement of muscular diseases such as sarcopenia. However, it is a great physical burden for elderly persons or in recuperation after an illness to positively practice high intensity exercise. Also, appropriate expert's instruction is necessary at the time of such exercise. Therefore, a nutritional approach that can be easily practiced even by a person with lowered basic physical strength or motor function is desired for the prevention or improvement of sarcopenia.

Examples that have been reported to improve muscle function and expected to prevent or improve muscular diseases such as sarcopenia include a muscular atrophy inhibitor comprising proanthocyanidin as an active ingredient (Patent Literature 1); an inhibitor of muscular fiber type shifting comprising a fruit-derived polyphenol as an active ingredient, which suppresses muscle fiber type shifting in disuse muscle atrophy (Patent Literature 2); and a muscle dysfunction inhibitor comprising catechin as an active ingredient (Patent Literature 3). Moreover, prevention or early recovery of skeletal muscle atrophy by intake of proteins and amino acids has been studied. However, no muscular atrophy-suppressing effect of a particular dipeptide or tripeptide has been yet reported.

CITATION LIST

Patent Literature

Patent Literature 1: Japanese Patent Laid-Open No. 2002-338464
Patent Literature 2: Japanese Patent Laid-Open No. 2006-328031
Patent Literature 3: Japanese Patent. Laid-Open No. 2008-13473

SUMMARY

Technical Problem

An object of the present invention is to provide a composition capable of suppressing muscular atrophy.

Solution to Problem

The present invention provides a composition for suppressing muscular atrophy, comprising as an active ingredient(s) one or more peptides selected from
the group consisting of tripeptides DIY, TYN, YNP, NPQ, DFY, DIF, FYN, IFN, FNP, and NPK;
the group consisting of dipeptides comprising F; and
the group consisting of dipeptides DI, IY, YN, and NP.

Effects of Invention

The composition of the present invention suppresses muscular atrophy and consequently low muscle mass. The composition of the present invention is useful in the prevention or treatment of a disease with muscular atrophy such as sarcopenia or disuse muscle atrophy, in the improvement of low muscle mass or muscle weakness, and the improvement of urine leakage.

DESCRIPTION OF EMBODIMENTS

Figure 1:
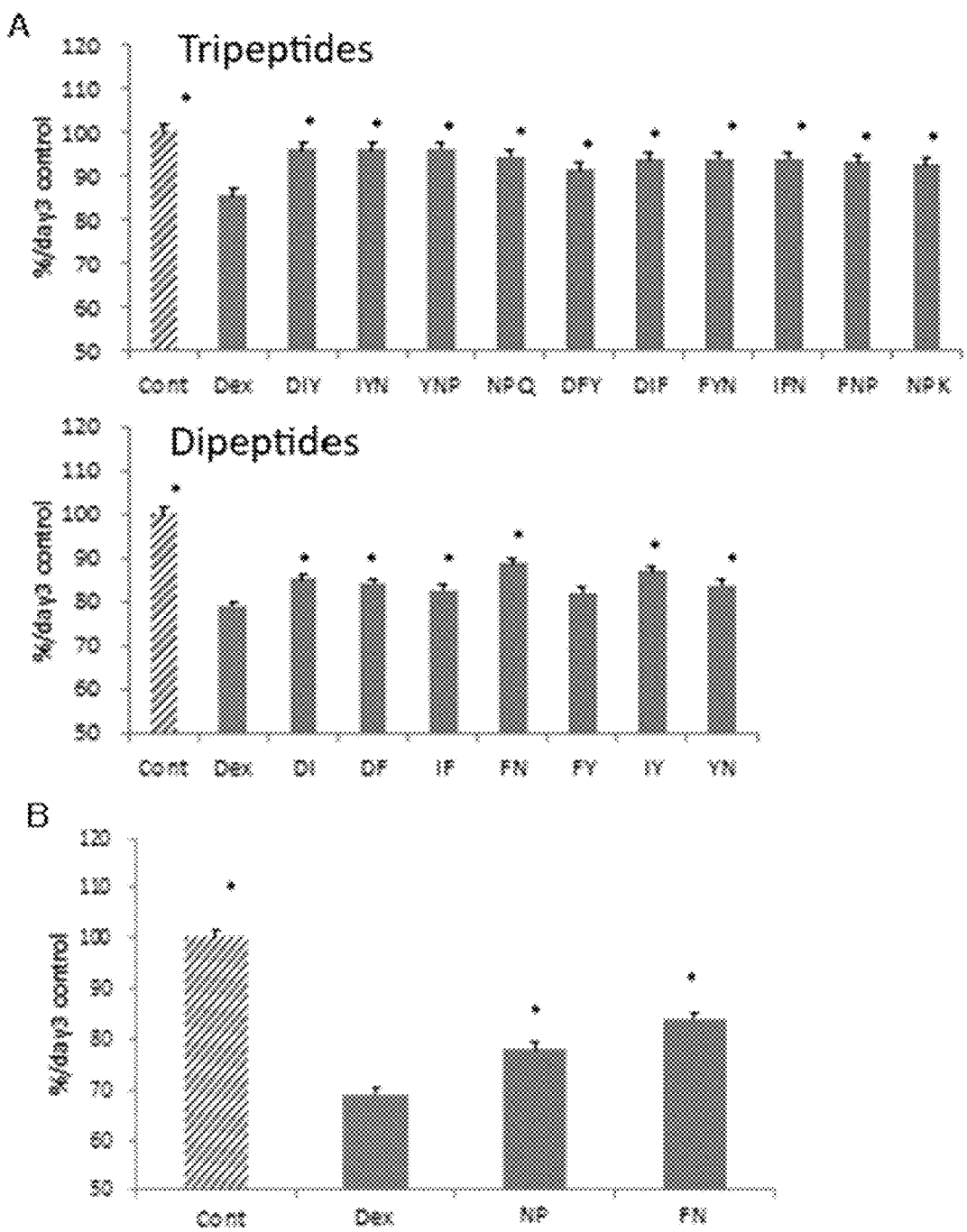
FIG. 1 illustrates the suppression of muscular atrophy by a dipeptide or tripeptide in a murine skeletal muscle cell line. Panel A illustrates the results of 17 peptides and Panel B illustrates the results of additional experiments with FN and NP. Cent: Control, Dex: dexamethasone. *$p<0.05$ (vs. dexamethasone).

In the present disclosure, amino acid residues may be represented with the following abbreviations.
Ala or A: alanine residue
Arg or A: arginine residue
Asn or N: asparagine residue
Asp or D: aspartic acid residue
Cys or C: cysteine residue
Gin or Q: glutamine residue Glu or E: glutamic acid residue
Gly or G: glycine residue
His or H: histidine residue
Ile or I: isoleucine residue
Leu or L: leucine residue
Lys or K: lysine residue
Met or M: methionine residue
Phe or F: phenylalanine residue
Pro or P: proline residue
Ser or S: serine residue
Thr or T: threonine residue
Trp or K: tryptophan residue
Tyr or Y: tyrosine residue
Val or V: valine residue The term "peptide" as used herein is a generic name of peptides encompassing dipeptides, tripeptides, and longer peptides (having four or more amino acid residues) and may mean any of these peptides depending on the context.

The composition for suppressing muscular atrophy according to the present invention comprises as an active ingredient(s) one or more peptides selected from
the group consisting of tripeptides DIY, IYN, YNP, NPQ, DFY, DIF, FYN, IFN, FNP, and NPK;
the group consisting of dipeptides comprising F; and
the group consisting of dipeptides DI, IY, YN, and NP.

In an embodiment, the one or more peptides are selected from the group consisting of dipeptides comprising F. In other words, the composition for suppressing muscular atrophy according to the present invention in this embodiment comprises as an active ingredient(s) one or more peptides selected from the group consisting of dipeptides comprising F. As used herein, the term "dipeptide comprising F" refers to a dipeptide in which one of the amino acid residues composing the dipeptide is phenylalanine (F). Specific examples of such a dipeptide include FA, FR, FN, FD, EC, FQ, FE, FG, FH, FI, FL, FK, FM, FF, FP, FS, FT, FW, FY, FV, AF, RF, NE, DF, CF, QF, EF, GF, HF, IF, LF, KF, MF, PF, SF, TF, WF, YF, and VF. Among these, FN is preferred.

In an embodiment, the one or more peptides are selected from
the group consisting of tripeptides DIY, IYN, YNP, NPQ, DFY, DIE, FYN, IFN, FNP, and NPK; and
the group consisting of dipeptides DI, DF, IF, FN, FY, IY, YN, and NP. In other words, the composition for suppressing muscular atrophy according to the present invention in this embodiment comprises as an active ingredient(s) one or more peptides selected from
the group consisting of tripeptides DIY, IYN, YNP, NPQ, DFY, DIF, FYN, IFN, FNP, and NPK; and
the group consisting of dipeptides DI, DF, IF, FN, FY, IY, YN, and NP.

The composition according to the present invention may comprise one peptide or two or more peptides selected from the group of the tripeptides and/or the dipeptides. When the composition according to the present invention comprises two or more peptides, the peptides may be contained in a single formulation or separate formulations. When the peptides are contained in separate formulations, the dosage forms and the routes of administration of the formulations may be the same or different.

In an embodiment, the composition according to the present invention comprises as an active ingredient(s) only one or more peptides selected from the group of the tripeptides and/or the dipeptides (in other words, the composition does not comprise any active ingredient other than the one or more peptides). In a further embodiment, the composition according to the present invention comprises as an active ingredient only one peptide (for example, FN or DF) selected from the group of the tripeptides and/or the dipeptides (in other words, it does not comprise any active ingredient other than the peptide).

The dipeptides and tripeptides can be produced by a method commonly used in the art, such as fermentation, enzymatic treatment, or chemical synthesis. For example, a dipeptide or tripeptide may be obtained by hydrolyzing with an appropriate protease a protein or peptide containing the amino acid sequence of the peptide of interest, and separating and purifying the product using a technique such as column chromatography. Alternatively, a dipeptide or tripeptide may be synthesized by a method for peptide synthesis described in references such as Peptide Synthesis, Interscience, New York, 1966; The Proteins, vol. 2, Academic Press Inc., New York, 1976; Peptide Synthesis (in Japanese), Maruzen Co., Ltd., 1975; Basics and Experiments of Peptide Synthesis (in Japanese), Maruzen Co., Ltd., 1985; and Development of Pharmaceuticals, the Sequel (in Japanese), vol. 14, Peptide Synthesis, Hirokawa-Shoten Ltd., 1991.

The muscular atrophy refers to a condition wherein muscle becomes thin, which results in decrease of muscle mass. Therefore, the composition according to the present invention may be a composition for suppressing decrease of muscle mass or a composition for suppressing muscle weakness. The composition according to the present invention is useful for the prevention or treatment or the improvement of muscular atrophy or low muscle mass, and may be used for any subject for which the prevention or treatment or the improvement of muscular atrophy or low muscle mass is required or desired.

In an embodiment, the composition according to the present invention is used in the prevention or treatment of a disease with muscular atrophy. Examples of the disease include sarcopenia, disuse muscle atrophy, muscular dystrophy, diabetic amyotrophy, cachexia, steroid myopathy, drug induced myopathy, rhabdomyolysis, myasthenia gravis, amyotrophic lateral sclerosis, Charcot-Marie-Tooth disease, and stress urinary incontinence.

In a further embodiment, the composition according to the present invention is used in the improvement of muscular atrophy, and consequently the improvement of low muscle mass or muscle weakness. For example, the composition according to the present invention may be used for the maintenance of muscle on old age or the improvement of urine leakage.

In an embodiment, the composition according to the present invention may be a pharmaceutical product or quasi-pharmaceutical product for humans or animals. The pharmaceutical product or quasi-pharmaceutical product may comprise a pharmaceutically acceptable carrier and/or additive such as a stabilizing agent, an antiseptic, a solubilizer, a pH adjuster, a thickener, an antioxidant, a colorant, a flavor, or an artificial sweetener in addition to the peptide(s) as an active ingredient(s).

The pharmaceutical product or quasi-pharmaceutical product may be administered via an enteral route or via a parenteral route. Examples of the enteral route include oral route and tubal feeding. Examples of the parenteral route include nasal, pulmonary, intravenous, transdermal, and intramuscular routes.

The pharmaceutical product or quasi-pharmaceutical product may be formulated into a desired dosage form as appropriate depending on the mode of administration such as oral administration or parenteral administration. The dosage form is not particularly limited to, but may be, for oral administration, for example, a solid formulation such as powder, granules, tablets, troches, or capsules; and a liquid such as a solution, syrup, suspension, or emulsion. For parenteral administration, the pharmaceutical product or quasi-pharmaceutical product may be formulated into, for example, a suppository, an air spray, an inhalant, an ointment, a patch, or an injection (including an infusion). The composition according to the present invention may be a freeze-dried formulation that can be reconstituted with a liquid such as sterile water before use. The composition according to the present invention can be formulated by a known method depending on the dosage form as appropriate.

In a further embodiment, the composition according to the present invention may be a food or drink, for example, a general food or drink for humans or animals, a health food, a functional food, a food for invalids, an enteral food, a food for a special dietary use, a functional health food, a food for a specified health use, a food with a function claim, or a functional nutritional food, that utilizes the effect of improving muscular atrophy or low muscle mass by suppression of muscular atrophy. The food or drink may be prepared by adding the peptide to a known food or drink, or a food or drink newly produced by admixing the peptide to its raw materials. The food or drink may be one to be added to another food or drink.

The food or drink may be in any form such as liquid, paste, solid, or powder. The food or drink may be a supplement in a form of tablets, capsules, granules, powders, fine granules, chews, syrup, or oral solution (such as suspension or emulsion), or may be a fluid food. The food or drink may also be in a form of a usual food or drink, for example, confectionery (such as cookie, biscuit, chocolate, chips, cake, gum, candy, gummy candy, steamed bun, yokan, pudding, jelly, yogurt, ice cream, or sherbet), bread, noodle, rice, cereal food, drink (such as liquid formulation, refreshing beverage, carbonated drink, nutrition beverage, powdered beverage, fruit juice, milk drink, or jelly drink), soup (powdered, freeze-dried), or miso soup (powdered, freeze-dried).

The food or drink may be provided or sold as a food or drink with a claim of a specified use (especially for health use) or a function. The "claim" may be made by any action to inform the consumer of the above use, and includes any expression by which one can recall or expect the above use regardless of the purpose of the claim, contents of the claim, the object or medium on which the claim is displayed, or other factors.

The "claim" is preferably made by the way that consumers can directly recognize the use. Specifically, the claim may be made by an act of transferring, delivering, or displaying for transferring or delivering, or importing a product related to the food or drink stating the use on its own or its wrapping; an act of displaying or distributing an advertisement, a price list, or a transaction document for the product stating the use, or providing such information with stating the use by an electromagnetic way (such as the Internet).

The claim is preferably a claim approved by an entity such as the government (for example, a claim approved based on the various systems established by the government and made in a manner based on such approval). Such a claim is preferably attached to wrapping, a container, a catalogue, a pamphlet, an advertising material on sales site such as POP, or other documents for example.

As used herein, the food or drink "for improving low muscle mass" may be a food or drink with a claim that recalls "improvement of low muscle mass", such as a claim "maintenance of muscle on old age" or "support of activity for making muscle".

As used herein, the food or drink for the "improvement of stress urinary incontinence" or "improvement of urine leakage" may be a food or drink with a claim that recalls "stress urinary incontinence" or "urine leakage", such as a claim "for those feeling not refreshed", "for those feeling unrestful", "for those not confident in going out in the night or for a long time", or "for those feeling anxious at straining oneself, coughing or sneezing, etc.".

The dose or intake per day of the dipeptide or tripeptide contained in the composition according to the present invention is determined as appropriate depending on a factor (s) such as age and body weight of the subject, symptoms, or route of administration, and may be, for example, 50 mg to 20 g, preferably 70 mg to 5 g, and more preferably 100 mg to 3 g for each peptide. The daily dose of the peptide may be administered or taken at once or divided into several doses. The composition according to the present invention may be administered or taken every day or at several days intervals and the duration of the administration or intake is not particularly limited either.

Followings are provided by the present invention, for example.

1. A composition for suppressing muscular atrophy, comprising as an active ingredient(s) one or more peptides selected from
   the group consisting of tripeptides DIY, IYN, YNP, NPQ, DFY, DIF, FYN, IFN, FNP and NPK;
   the group consisting of dipeptides comprising F; and
   the group consisting of dipeptides DI, IY, YN, and NP.
2. The composition according to item 1, wherein the one or more peptides are selected from the group consisting of dipeptides comprising F.
3. The composition according to item 1, wherein the one or more peptides are selected from
   the group consisting of tripeptides DIY, IYN, YNP, NPQ, DFY, DIF, FYN, IFN, FNP, and NPK; and
   the group consisting of dipeptides DI, DE, IF, FN, FY, IY, YN, and NP.
4. The composition according to any one of items 1 to 3, wherein the one or more peptides comprise FN.
5. The composition according to any one of items 1 to 4, wherein the one or more peptides comprise DF.
6. The composition according to any one of items 1 to 5, for preventing or treating a disease with muscular atrophy.
7. The composition according to item 6, wherein the disease is sarcopenia, disuse muscle atrophy, muscular dystrophy, diabetic amyotrophy, cachexia, steroid myopathy, drug induced myopathy, rhabdomyolysis, myasthenia gravis, amyotrophic lateral sclerosis, Charcot-Marie-Tooth disease, or stress urinary incontinence.
8. The composition according to any one of items 1 to 7, wherein the composition is a pharmaceutical product.
9. A composition for improving low muscle mass, comprising as an active ingredient(s) one or more peptides selected from
   the group consisting of tripeptides DIY, IYN, YNP, NPQ, DFY, DIF, FYN, IFN, FNP, and NPK;
   the group consisting of dipeptides comprising F; and
   the group consisting of dipeptides DI, IY, YN, and NP.
10. The composition according to item 9, wherein the one or more peptides are selected from the group consisting of dipeptides comprising F.
11. The composition according to item 9, wherein the one or more peptides are selected from the group consisting of tripeptides DIY, IYN, YNP, NPQ, DFY, DIP, FYN, ITN, FNP, and NPK; and
the group consisting of dipeptides DI, DF, IF, FN, FY, IY, YN, and NP.

12. The composition according to any one of items 9 to 11, wherein the one or more peptides comprise FN.
13. The composition according to any one of items 9 to 11, wherein the one or more peptides comprise DF.
14. The composition according to any one of items 9 to 13, for improving stress urinary incontinence.
15. The composition according to any one of items 9 to 13, for improving urine leakage.
16. The composition according to any one of items 9 to 15, wherein the composition is a food or drink.
17. A therapeutic or non-therapeutic method for suppressing muscular atrophy or improving the decrease of muscle mass, comprising administering to a subject in need thereof one or more peptides selected from
the group consisting of tripeptides DIY, IYN, YNP, NPQ, DFY, DIF, FYN, IFN, FNP, and NPK;
the group consisting of dipeptides comprising F; and the group consisting of dipeptides DI, IY, YN, and NP.
18. Use of one or more peptides selected from
the group consisting of tripeptides DIY, IYN, YNP, NPQ, DFY, DIF, FYN, IFN, FNP, and NPK;
the group consisting of dipeptides comprising F; and
the group consisting of dipeptides DI, IY, YN, and NP, for the manufacture of a composition for suppressing muscular atrophy or a composition for improving low muscle mass.
19. Therapeutic or non-therapeutic use of one or more peptides selected from
the group consisting of tripeptides DIY, IYN, YNP, NPQ, DFY, DIF, FYN, IFN, FNP, and NPK;
the group consisting of dipeptides comprising F; and
the group consisting of dipeptides DI, IY, YN, and NP, for suppressing muscular atrophy or improving the decrease of muscle mass.

The present invention is further described by the following examples, but not limited by these examples in any sense.

EXAMPLE 1

Suppression of Muscular Atrophy in Murine Skeletal Muscle Cell Line

A murine skeletal muscle cell line (C2C12) was passaged and maintained in DMEM supplemented with 10% FES under conditions at 37° C. and 5% $CO_2$. The basal medium was 500 mL of DMEM (Sigma-Aldrich) supplemented with 12.5 mL of HEPES (Gibco), 5.5 mL of penicillin-streptomycin (Gibco), and 55 mL of fetal bovine serum (FBS, Sigma-Aldrich). The differentiation medium was DMEM supplemented with 12.5 mL of HEPES, 5.5 mL of penicillin-streptomycin, and 12.5 mL of horse serum (HS, SAFC Bioscience).

C2C12 was seeded at $5 \times 10^5$ cells/dish in 6 cm dishes (AGC TECHNO GLASS CO., LTD.) and cultured in the basal medium for 2 days. Subsequently, the culture was induced to differentiate in the differentiation medium. Five days after the start of the induction, the medium was changed into each differentiation medium to which each one of the peptides (17 peptides: DIY, IYN, YNP, NPQ, DFY, DIF, FYN, IFN, FNP, NPK, DI, DF, IF, FN, FY, IY, YN: MEDICAL & BIOLOGICAL LABORATORIES CO., LTD.) was added at 625 nM, and the culture was kept for 1 hour. Then, each medium was changed into a corresponding differentiation medium containing 625 nM of the same peptide and 10 µM dexamethasone (Dex) (Wako Pure Chemical Industries, Ltd.) and the same medium change was repeated every 24 hours for 3 days. The muscle diameter was determined by taking photographs of myotube cells of each group using BZ-9000 (KEYENCE) and converting the cell images into numerical values by the BZ-II image analysis application (KEYENCE). The muscle diameter was expressed in percentage relative to the muscle diameter of the control group (no dexamethasone added) on Day 3, which was defined to be 100%. Similarly, additional experiments were conducted on FN and NP. Furthermore, the muscle diameter was measured when each one of FN and LR (random dipeptide) was added at a concentration of 100 nM.

Figure 2:
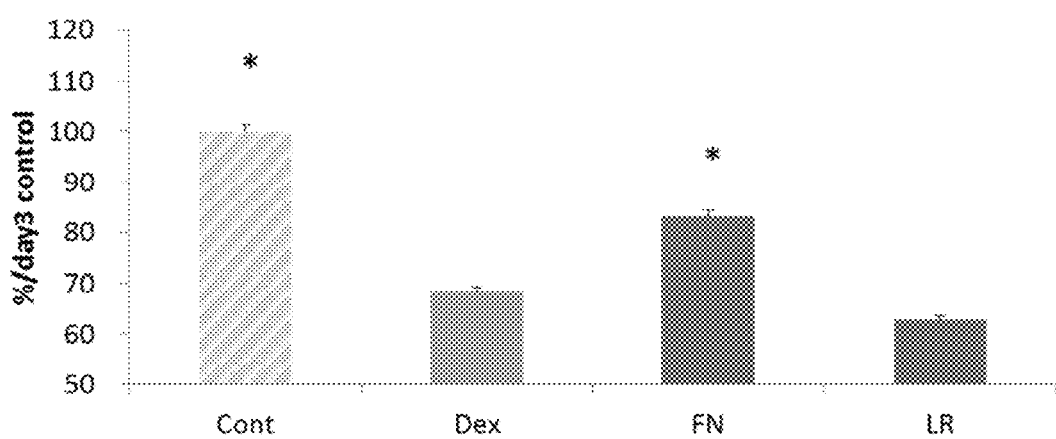
FIG. 2 illustrates the effect of FN or LR (added at 100 nM) on muscular atrophy in a murine skeletal muscle cell line. Cont: Control, Dex: dexamethasone. *$p<0.05$ (vs. dexamethasone).

17 tri and dipeptides (DIY, IYN, YNP, NPQ, DFY, DIF, FYN, IFN, FNP, NPK, DI, DF, IF, FN, IY, YN, and NP) provided significantly higher muscle diameters than the dexamethasone alone group and one peptide FY showed a similar tendency (FIG. 1, Panels A and B). In studies at the concentration of 100 nM, the muscle diameter with FN was significantly higher than that of the dexamethasone alone group, while no significant difference was found with LR (FIG. 2).

EXAMPLE 2

Suppression of Muscular Atrophy in Animal Model

C57BL/6J mice (male, 7 weeks old) were divided into 4 groups (control group, atrophy group, atrophy+FN group, atrophy+DF group) so that the body weight in each group was equal. The control group and the atrophy group were provided with sterile water and the atrophy+FN group and the atrophy+DF group were provided with an aqueous solution containing each peptide (1.4 mg/ml) ad libitum by a water supply bottle for 14 days. Muscular atrophy was introduced in the atrophy group, the atrophy+FN group, and the atrophy+DF group by intraperitoneal administration of 10 mg/kg dexamethasone (Sigma-Aldrich) once a day from Day 8 of watering ad libitum. After 7 days of dexamethasone administration and subsequent 12 hours of fasting, the animals were dissected. The anterior tibial muscles of both legs were excised under isoflurane anesthesia and the muscular fiber cross-sectional area (CSA) of the anterior tibial muscles and the expression of Atrogin-1, which is a marker protein for muscular atrophy, were measured.

Figure 3:
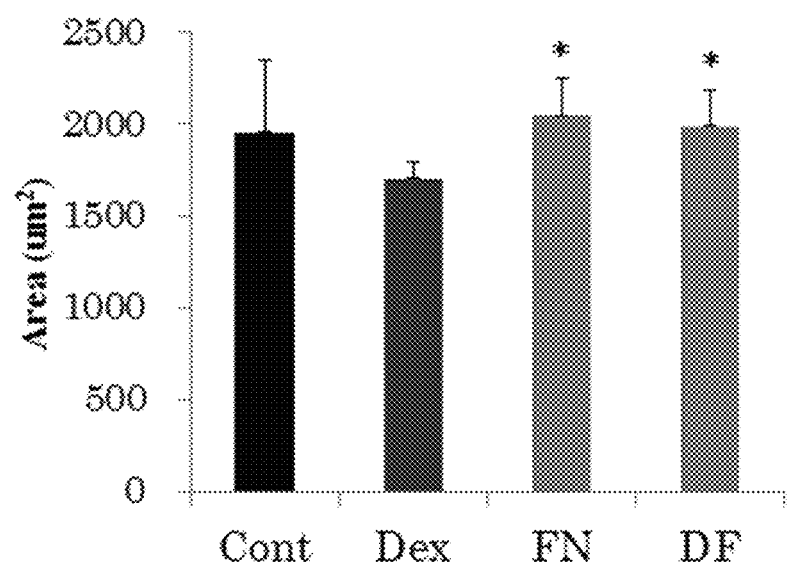
FIG. 3 illustrates the suppression of muscular atrophy by a dipeptide in an animal model. Cont: Control, Dex: dexamethasone. *$p<0.05$ (vs. dexamethasone).
Figure 4:
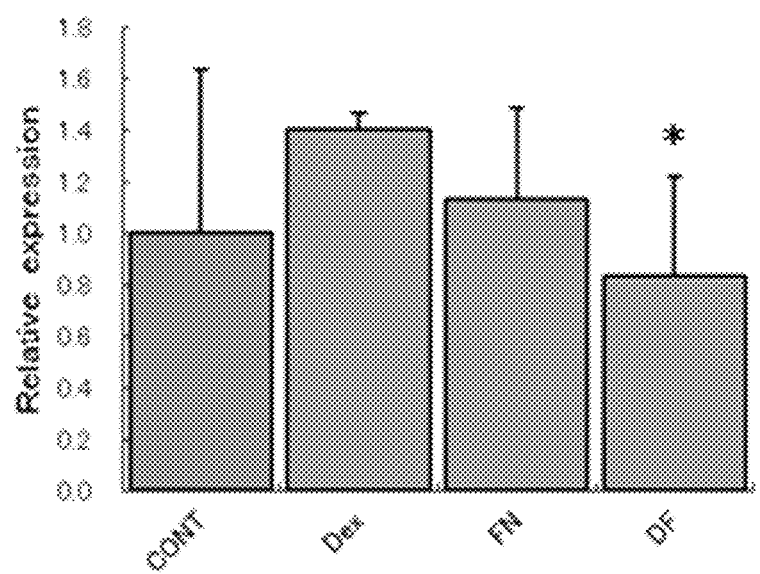
FIG. 4 illustrates the effect of a dipeptide on the expression of Atrogin-1 in an animal model. CONT: Control, Dexo: dexamethasone. *$p<0.05$ (vs. dexamethasone).

The CSA of the anterior tibial muscles was significantly higher in the atrophy+FN group and the atrophy+DF group than in the atrophy group (FIG. 3). Moreover, the expression of Atrogin-1 protein in the anterior tibial muscles showed a tendency to be lower in the atrophy+FN group than in the atrophy group, and was significantly lower in the atrophy+DF group than in the atrophy group (FIG. 4).

These results suggest that dipeptides comprising phenylalanine (F) are effective in the suppression of muscular atrophy since the effect was confirmed both in Examples 1 and 2. In particular, FN is shown to have a prominent effect since FN demonstrated a significant improvement in both muscle diameter and CSA and these results directly indicate the suppression of muscular atrophy.

The invention claimed is:
1. A method for suppressing muscular atrophy, comprising administering to a subject in need thereof one or more peptides selected from
the group consisting of tripeptides DIY, IYN, YNP, NPQ, DFY, DIF, FYN, IFN, FNP, and NPK; and the group consisting of dipeptides DI, IF, FN, FY, IY, YN, and NP.

2. The method according to claim 1, wherein the one or more peptides comprise FN.

3. The method according to claim 1, for treating a disease with muscular atrophy.

4. The method according to claim 3, wherein the disease is sarcopenia, disuse muscle atrophy, muscular dystrophy, diabetic amyotrophy, cachexia, steroid myopathy, drug induced myopathy, rhabdomyolysis, myasthenia gravis, amyotrophic lateral sclerosis, Charcot-Marie-Tooth disease, or stress urinary incontinence.

5. The method according to claim 1, wherein the one or more peptides are comprised in a pharmaceutical product.

6. The method according to claim 1, wherein the one or more peptides are included in a food or drink.

7. A method for improving low muscle mass, comprising administering to a subject in need thereof one or more peptides selected from
   the group consisting of tripeptides DIY, IYN, YNP, NPQ, DFY, DIF, FYN, IFN, FNP, and NPK; and
   the group consisting of dipeptides DI, IF, FN, FY, IY, YN, and NP.

8. The method according to claim 7, wherein the one or more peptides comprise FN.

9. The method according to claim 7, for improving stress urinary incontinence.

10. The method according to claim 7, for improving urine leakage.

11. The method according to claim 7, wherein the one or more peptides are comprised in a food or drink.

* * * * *